United States Patent

Rault et al.

[11] Patent Number: 6,071,945
[45] Date of Patent: Jun. 6, 2000

[54] 8H-THIENO-[2,3-B]PYRROLIZIN-8-ONE COMPOUNDS

[75] Inventors: Sylvain Rault, Moult; Cécile Enguehard, Caen; Jean-Charles Lancelot, Le Bourg; Max Robba, Paris; Ghanem Atassi, Saint Cloud; Alain Pierre, Les Alluets le Roi; Daniel-Henri Caignard, Le Pecq; Pierre Renard, Le Chesnay, all of France

[73] Assignee: Adir et Compagnie, Courbevoie, France

[21] Appl. No.: 09/361,064

[22] Filed: Jul. 26, 1999

[30] Foreign Application Priority Data

Jul. 27, 1998 [FR] France .................... 98.09552

[51] Int. Cl.[7] ............... A61K 31/407; C07D 495/14
[52] U.S. Cl. ................................. 514/411; 548/428
[58] Field of Search .................. 548/428; 514/411

[56] References Cited

U.S. PATENT DOCUMENTS

| | | | |
|---|---|---|---|
| 5,627,203 | 5/1997 | Rault et al. | 514/411 |
| 5,670,492 | 9/1997 | Amishiro et al. | 514/63 |
| 5,705,498 | 1/1998 | Gaster et al. | 514/214 |
| 5,801,174 | 9/1998 | Moldt et al. | 514/253 |

Primary Examiner—Joseph McKane
Assistant Examiner—Sonya Wright
Attorney, Agent, or Firm—The Firm of Gordon W. Hueschen

[57] ABSTRACT

A compound selected from those of formula (I):

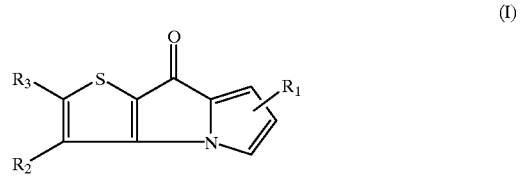

wherein:

$R_1$ represents hydrogen, halogen, alkyl, nitro, hydroxy, alkoxy, trihaloalkyl, trihaloalkoxy or optionally substituted amino, $R_2$ represents optionally substituted aryl or heteroaryl, $R_3$ represents hydrogen, halogen, alkyl, nitro, hydroxy, alkoxy, trihaloalkyl, trihaloalkoxy or optionally substituted amino, their isomers and addition pharmaceutically-acceptable acid or base salts thereof and medicinal products containing the same are useful in the treatment of cancer.

8 Claims, No Drawings

8H-THIENO-[2,3-B]PYRROLIZIN-8-ONE COMPOUNDS

FIELD OF THE INVENTION

The present invention relates to new 8H-thieno-[2,3-b] pyrrolizin-8-one compounds.

DESCRIPTION OF THE PRIOR ART

The needs of anti-cancer therapeutics demand the constant development of new anti-tumour agents with the aim of obtaining medicaments that are both more active and better tolerated. More particularly, solid tumours pose a major problem for anti-cancer chemotherapy in view of their intrinsic and/or acquired resistance to existing products.

Apart from the fact that they are new, the compounds of the invention exhibit surprising and particular activity in vivo and in vitro. The compounds discovered by the Applicant have anti-tumour properties which make them especially valuable in the treatment of cancers and, advantageously, in the treatment of solid tumours.

Compounds having closely related structures have been described in the literature, especially in Patent Application EP 718 299, those compounds being used as synthesis intermediates for obtaining tricyclic oxime ethers. No therapeutic activity is described for those synthesis intermediates, although the final products, that is to say the tricyclic oxime ethers, have a very strong affinity for $5HT_{2C}$ and/or $5HT_3$ receptors—a therapeutic area that is different to that of the present invention.

DETAILED DESCRIPTION OF THE INVENTION

More specifically, the present invention relates to the compounds of formula (I):

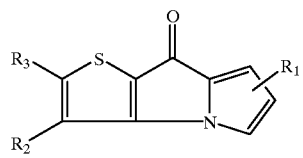

(I)

wherein:
R$_1$ represents a hydrogen atom, a halogen atom, a linear or branched ($C_1$–$C_6$)alkyl group, a nitro (group, a hydroxy group, a linear or branched ($C_1$–$C_6$)alkoxy group, a linear or branched ($C_1$–$C_6$)trihaloalkyl group, a linear or branched ($C_1$–$C_6$)trihaloalkoxy group, or an amino group (optionally substituted by one or two linear or branched ($C_1$–$C_6$)alkyl groups, which may be identical or different, each independently of the other),
R$_2$ represents an optionally substituted aryl group or an optionally substituted heteroaryl group,
R$_3$ represents a hydrogen atom, a halogen atom, a linear or branched ($C_1$–$C_6$)alkyl group, a nitro group, a hydroxy group, a linear or branched ($C_1$–$C_6$)alkoxy group, a linear or branched ($C_1$–$C_6$)trihaloalkyl group, a linear or branched ($C_1$–$C_6$)trihaloalkoxy group, or an amino group (optionally substituted by one or two linear or branched ($C_1$–$C_6$)alkyl groups, which may be identical or different, each independently of the other), to isomers thereof and addition salts thereof with a pharmaceutically acceptable acid or base, with the proviso that, when R$_1$ and R$_3$ simultaneously represent a hydrogen atom, R$_2$ cannot represent a phenyl group optionally substituted in the para position by a bromine atom, chlorine atom, fluorine atom, methoxy group or hydroxy group.

Among the pharmaceutically acceptable acids there may be mentioned, without implying any limitation, hydrochloric, hydrobromic, sulphuric, phosphonic, acetic, trifluoroacetic, lactic, pyruvic, malonic, succinic, glutaric, fumaric, tartaric, maleic, citric, ascorbic, oxalic, methanesulphonic, camphoric acid etc., Among the pharmaceutically acceptable bases there may be mentioned, without implying any limitation, sodium hydroxide, potassium hydroxide, triethylamine, tert-butylamine etc.

An aryl group is understood as being a phenyl, naphthyl, dihydronaphthyl, tetrahydronaphthyl, indenyl or indanyl group; a heteroaryl group is understood as being a mono- or bi-cyclic aromatic group having from 5 to 12 members and containing one, two or three hetero atoms, which may be identical or different, selected from oxygen, nitrogen and sulphur. Among, those heteroaryl groups there may be mentioned, without implying any limitation, the thienyl, furyl, pyrrolyl, pyridyl and indolyl groups; optionally substituted is understood as referring to an aryl or heteroaryl group as defined hereinbefore optionally substituted by one or more groups, which may be identical or different, each selected independently of the other(s) from halogen, linear or branched ($C_1$–$C_6$)alkyl, hydroxy, linear or branched ($C_1$–$C_6$)alkoxy, linear or branched ($C_1$–$C_6$)trihaloalkoxy, nitro, cyano, amino, linear or branched ($C_1$–$C_6$)alkylamino, di-($C_1$–$C_6$)alkylamino in which each alkyl group may be linear or branched, linear or branched ($C_1$–$C_6$)acyl, aminocarbonyl (the amino moiety being optionally substituted by one or two linear or branched ($C_1$–$C_6$)alkyl groups, which may be identical or different), carboxy, linear or branched ($C_1$–$C_6$)alkoxycarbonyl, methylenedioxy, ethylenedioxy, linear or branched ($C_1$–$C_6$)alkylcarbonyloxy, and aryl-($C_1$–$C_6$)alkoxy in which the alkoxy moiety may be linear or branched.

The preferred substituent R$_2$ according to the invention is phenyl substituted by at least one group as defined hereinbefore.

According, to an advantageous variant of the invention, the preferred substituent R$_2$ is phenyl substituted by at least one group selected from hydroxy, linear or branched ($C_1$–$C_6$)alkoxy, and linear or branched ($C_1$–$C_6$) alkylcarbonyloxy.

The preferred substituents R$_1$ and R$_3$ according to the invention are in each case a hydrogen atom.

The preferred compounds according to the invention are 3-(3,4-dihydroxyphenyl)-8H-thieno[2,3-b]pyrrolizin-8-one and 2-methoxy-5-(8-oxo-8H-thieno[2,3-b]pyrrolizin-3-yl) phenyl acetate.

The isomers of the preferred compounds and also the addition salts thereof with a pharmaceutically acceptable acid or base are an integral part of the invention.

The invention relates also to a process for the preparation of the compounds of formula (I), which process is characterised in that there is used as starting material a compound of formula (II):

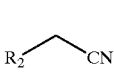

(II)

wherein R$_2$ is as defined for formula (I), which compounds of formula (II) are reacted, in the presence of an alkali metal, with ethyl formate to yield the compounds of formula (III):

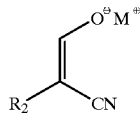
(III)

wherein $R_2$ is as defined hereinbefore and $M^+$ represents an alkali metal cation, such as the sodium or potassium cation, which compounds of formula (III) are placed in conditions of nucleophilic addition in the presence of phenylsulphonyl chloride to yield the compounds of formula (IV):

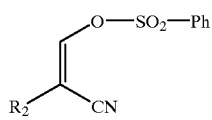
(IV)

wherein $R_2$ is as defined hereinbefore, which compounds of formula (IV) are reacted with methyl thioglycolate to yield the compounds of formula (V):

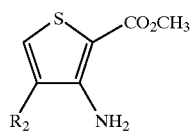
(V)

wherein $R_2$ is as defined hereinbefore, the amino group of which compounds of formula (V) is protected according to conventional methods of organic synthesis and which are then reacted with a compound of formula (VI):

(VI)

wherein X represents a leaving group and $R_3$ is as defined for formula (I), the amino function of which is then deprotected to yield the compounds of formula (VII):

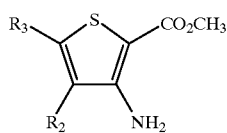
(VII)

wherein $R_2$ and $R_3$ are as defined for formula (I), which compounds of formula (VII) are placed in the presence of dimethoxytetrahydrofuran and 4-chloropyridinium chloride to yield the compounds of formula (VIII):

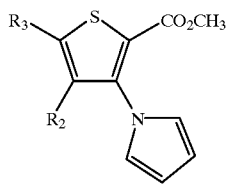
(VIII)

wherein $R_2$ and $R_3$ are as defined hereinbefore,
which are then reacted with pyrrolidine to yield the compounds of formula (IX):

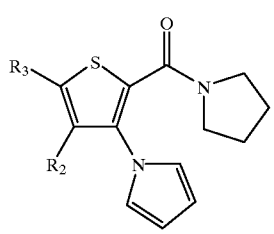
(IX)

wherein $R_2$ and $R_3$ are as defined hereinbefore,
which compounds of formula (IX) are cyclised using phosphorus oxychloride to yield the compounds of formula (I/a), a particular case of the compounds of formula (I):

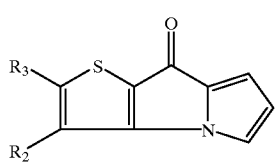
(I/a)

wherein $R_2$ and $R_3$ are as defined hereinbefore,
the pyrrole nucleus of which compounds of formula (I/a) is functionalised according to conventional conditions of organic synthesis to yield the compounds of formula (I/b), a particular case of the compounds of formula (I):

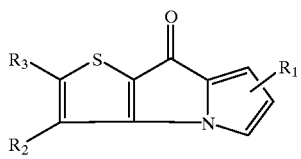
(I/b)

wherein $R_2$, $R_3$ and $R_1$ are as defined for formula (I) except that $R_1$ cannot represent a hydrogen atom,
the compounds (I/a) and (I/b) constituting the totality of the compounds of the invention, which, if necessary, are purified according to a conventional purification technique, if desired, may be separated into their different isomers according to a conventional separation technique and, where appropriate, are converted into their addition salts with a pharmaceutically acceptable acid or base.

The compounds of formulae (II) and (VI) are either commercially available or are obtained according to conventional methods of organic synthesis.

The compounds of formula (I) exhibit particularly interesting anti-tumour activities. They have excellent in vitro cytotoxicity on cell lines, especially lines produced starting from solid human tumours, and they are very well tolerated in vivo. The characteristic properties of these compounds allow them to be used in therapeutics as anti-tumour agents.

The present invention relates also to pharmaceutical compositions comprising the compounds of formula (I), optical isomers thereof or addition salts thereof with a pharmaceutically acceptable base or acid, alone or in combination with one or more pharmaceutically acceptable, inert, non-toxic excipients or carriers.

Among the pharmaceutical compositions according to the invention there may be mentioned more especially those that are suitable for oral, parenteral (intravenous, intramuscular or subcutaneous). per- or trans-cutaneous, nasal, rectal, perlingual, ocular or respiratory administration and especially tablets or dragees, sublingual tablets, soft gelatin capsules, hard gelatin capsules, suppositories, creams, ointments, dermal gels, injectable or drinkable preparations, eye or nose drops etc.

The useful dosage varies according to the age and weight of the patient, the route of administration, the nature and severity of the disorder and the administration of any associated treatments, and ranges from 1 mg to 500 mg in one or more administrations per day.

The Examples which follow illustrate the invention but do not limit it in any way. The starting materials used are materials that are known or that are prepared according to known procedures.

The various steps yield synthesis intermediates that are useful in the preparation of the compounds of the invention.

The structures of the compounds described in the Examples and in the synthesis steps have been determined according to customary spectrophotometric techniques (infrared, nuclear magnetic resonance, mass spectrometry . . . ).

EXAMPLE 1

3-(2-Methoxyphenyl)-8H-thieno[2,3-b]pyrrolizin-8-one

Step A: α-Hydroxymethylidene-(2-methophenyl)acetonitrile, sodium salt 1 equivalent of ethyl formate and 1 equivalent of 2-(2-methoxyphenyl)acetonitrile are added in succession to a solution, cooled to 0° C., of 0.34 mol of sodium in 150 ml of methanol. The reaction mixture is subsequently heated for one hour at 60° C. and then diluted by adding solvent, causing a new precipitate to appear, which is filtered off and then dried in vacuo, allowing the expected product to be isolated.

Melting Point: >250° C.

Step B: α-(Phenylsulphonyloxymethylidene)-2-methoxyphenylacetonitrile 1 equivalent of 2-methoxyphenyl-sulphonyl chloride is added dropwise to a suspension, cooled to 0° C., of 0.3 mol of the compound obtained in Step A in 100 ml of dimethylformamide. After 2 hours' stirring, 100 ml of water are added, bringing about the formation of a precipitate. The precipitate is filtered off and then dried in vacuo, allowing the expected product to be isolated.

Melting Point: >250° C.

Step C: Methyl 3-amino-4-(2-methoxyphenyl)-2-thiophenecarboxylate 11 mmol of sodium are dissolved in 100 ml of methanol. After cooling the reaction mixture using an ice bath, 4.5 mmol of methyl thioglycolate and then 3.7 mmol of the compound obtained in Step B are added. After 2 hours' reaction, 100 ml of water are added, bringing about the formation of a precipitate, which is filtered off and then dried, allowing the to expected product to be isolated.

Melting Point: 110° C.

Step D: Methyl 4-(2-methoxyphenyl)-3-(1H-1-pyrrolyl)-2-thiophenecarboxylate 5.2 mmol of dimethoxytetrahydrofuran and 5.2 mmol of 4-chloropyridinium chloride in 100 ml of dioxane are stirred for 15 minutes at ambient temperature and then 5.2 mmol of the compound obtained in Step C are added. The reaction mixture is then heated at reflux of the solvent for 3 hours and subsequently filtered. After concentrating the filtrate under reduced pressure, the residue obtained is crystallised by trituration in ethyl ether, allowing the expected product to be isolated.

Melting Point: 148° C.

Step E: 4-(2-Methoxyphenyl)-3-(1H-1-pyrrol)-2-thiophene-N-pyrrolidinocarboxamide A solution of 3.8 mmol of the compound obtained in Step D in 50 ml of pyrrolidine is heated at reflux for 3 hours. After cooling, 100 ml of water are added, bringing about the formation of a precipitate, which is filtered off, rinsed with petroleum ether and then dried in vacuo, allowing the expected product to be isolated.

Melting Point: 108° C.

Step F: 3-(2-Methoxyphenyl)-8H-thieno[2,3-b]pyrrolizin-8-one

A solution of 2.7 mmol of the compound obtained in Step E in 50 ml of phosphorus oxychloride is heated at reflux for 3 hours. After cooling and evaporating off the solvent under reduced pressure, the residue is crystallised from ether, filtered off and washed with petroleum ether. The crystals are then poured into 100 ml of 10% aqueous sodium hydroxide and stirred at 50° C. for 1 hour. The solid is subsequently filtered off, dried and then purified by chromatography on silica gel (chloroform), allowing the expected product to be isolated.

Melting Point: 142° C.

Elemental microanalysis:

|  | % C | % H | % N |
|---|---|---|---|
| calculated | 68.31 | 3.94 | 4.98 |
| found | 68.24 | 4.04 | 4.84 |

EXAMPLE 2

3-(3-Methoxyphenyl)-8H-thieno[2,3-b]pyrrolizin-8-one

The procedure is as in Example 1, Steps A to F, using 2-(3-methoxyphenyl)acetonitrile as substrate in Step A.

Melting Point: 150° C.

Elemental microanalysis:

|  | % C | % H | % N |
|---|---|---|---|
| calculated | 68.31 | 3.94 | 4.98 |
| found | 63.48 | 3.94 | 4.29 |

EXAMPLE 3

3-(3,4-Dimethoxyphenyl)-8H-thieno[2,3-b]pyrrolizin-8-one

The procedure is as in Example 1, Steps A to F, using 2-(3,4-dimethoxyphenyl)-acetonitrile as substrate in Step A.

Melting Point: 190° C.
Elemental microanalysis:

|  | % C | % H | % N |
|---|---|---|---|
| calculated | 65.58 | 4.21 | 4.50 |
| found | 64.45 | 4.12 | 4.46 |

EXAMPLE 4

3-(3,4-Methylenedioxyphenyl)8H-thieno[2,3-b]
pyrrolizin-8-one

The procedure is as in Example 1, Steps A to F, using the substrate used in Example 3 as substrate in Step A.
Melting Point: 168° C.
Elemental microanalysis:

|  | % C | % H | % N |
|---|---|---|---|
| calculated | 65.08 | 3.07 | 4.74 |
| found | 59.30 | 3.77 | 4.39 |

EXAMPLE 5

3-(3,4,5-Trimethoxyphenyl)-8H-thieno[2,3-b]
pyrrolizin-8-one

The procedure is as in Example 1, Steps A to F, using 2-(3,4,5-trimethoxyphenyl)acetonitrile as substrate in Step A.
Melting Point: 180° C.
Elemental microanalysis:

|  | % C | % H | % N |
|---|---|---|---|
| calculated | 63.33 | 4.43 | 4.10 |
| found | 63.26 | 4.86 | 4.22 |

EXAMPLE 6

3-(2-Hydroxyphenyl)-8H-thieno[2,3-b]pyrrolizin-8-one

A solution of 1.1 mmol of the compound of Example 1 and 1.1 mmol of boron tribromide in chloroform is stirred for 30 minutes at ambient temperature. After adding 100 ml of water, the precipitate formed is filtered off, dried and then recrystallised from ethanol, allowing the expected product to be isolated.
Melting Point: 192° C.
Elemental microanalysis:

|  | % C | % H | % N |
|---|---|---|---|
| calculated | 67.40 | 3.39 | 5.24 |
| found | 66.49 | 3.25 | 5.48 |

EXAMPLE 7

3-(3-Hydroxyphenyl)-8H-thieno[2,3-b]pyrrolizin-8-one

The procedure is as in Example 6, using the product obtained in Example 2 as substrate.
Melting Point: >260° C.
Elemental microanalysis:

|  | % C | % H | % N |
|---|---|---|---|
| calculated | 67.40 | 3.39 | 5.24 |
| found | 64.19 | 3.24 | 4.86 |

EXAMPLE 8

3-(3,4-Dihydroxyphenyl)-8H-thieno[2,3-b]
pyrrolizin-8-one

The procedure is as in Example 6, using the product obtained in Example 3 as substrate.
Melting Point: >260° C.

EXAMPLE 9

3-(4-Ethoxyphenyl)-8H-thieno[2,3-b]pyrrolizin-8-one

Step G: 3-(4-Methoxyphenyl)-8H-thieno[2,3-b]pyrrolizin-8-one

The product is obtained according to the operating conditions described in Patent Application EP 718 299.

Step H: 3-(4-Ethoxyphenyl)-8H-thieno[2,3-b]pyrrolizin-8-one 1.4 mmol of the compound obtained in Step G and 15 ml of ethyl bromide are added to a solution of 1.4 mmol of sodium in 100 ml of methanol. The reaction mixture is then heated until the substrate has completely disappeared according to thin-layer chromatography (dichloromethane/methanol:9/1). The solvent is subsequently evaporated off under reduced pressure and the solid obtained is then stirred into 0.5N aqueous sodium hydroxide. After filtration and washing with water, the crystals are dried and then recrystallised from a mixture of methanol/ethanol:1/2, allowing the expected product to be isolated.
Melting Point: 200° C.
Elemental microanalysis:

|  | % C | % H | % N |
|---|---|---|---|
| calculated | 69.13 | 4.44 | 4.74 |
| found | 69.07 | 4.44 | 4.96 |

EXAMPLE 10

3-(4-Propoxyphenyl)-8H-thieno[2,3-b]pyrrolizin-8-one

The procedure is as in Step H of Example 9, using n-propyl bromide as reagent. The product is recrystallised from a mixture of methanol/isopropanol:1/2.
Melting Point: 172° C.
Elemental microanalysis:

|  | % C | % H | % N |
|---|---|---|---|
| calculated | 69.88 | 4.89 | 4.53 |
| found | 69.06 | 4.65 | 4.87 |

EXAMPLE 11

3-(4-n-Butoxyphenyl8H-thieno[2,3-b]pyrrolizin-8-one

The procedure is as in Step H of Example 9, using n-butyl bromide as reagent. The product is recrystallised from ethanol.

Melting Point: 129° C.

Elemental microanalysis:

|  | % C | % H | % N |
|---|---|---|---|
| calculated | 70.56 | 5.30 | 4.33 |
| found | 69.84 | 5.28 | 4.65 |

EXAMPLE 12

6-Bromo-3-(4-methoxyphenyl)-8H-thieno[2,3-b]pyrrolizin-8-one 2.1 mmol of bromine are added to a solution of 1.8 mmol of 3-(4-methoxyphenyl)-8H-thieno[2.3-b]pyrrolizin-8-one in 50 ml of chloroform. After two hours' stirring the solvent is evaporated off under reduced pressure. Chromatography on silica gel (dichloromethane) allows the expected product to be isolated.

Melting Point: 186° C.

Elemental microanalysis:

|  | % C | % H | % N |
|---|---|---|---|
| calculated | 53.35 | 2.80 | 3.89 |
| found | 52.58 | 2.82 | 4.12 |

EXAMPLE 13

2,6Dibromo-2-(4-methoxyphenyl)-8-H-thieno[2,3-b]pyrrolizin-8-one

The product is isolated in the course of the chromatography on silica gel carried out on the compound of Example 12.

Melting Point: 202° C.

Elemental microanalysis:

|  | % C | % H | % N |
|---|---|---|---|
| calculated | 43.76 | 2.07 | 3.19 |
| found | 43.48 | 2.02 | 3.58 |

EXAMPLE 14

3-(3-Hydroxy-4-methoxyphenyl)-8H-thieno[2,3-b]pyrrolizin-8-one

A solution of 0.6 mmol of the compound of Example 3 and an excess of aluminium chloride in chloroform is stirred at 50° C. for 30 minutes. After concentration under reduced pressure, the residue is stirred in water for 30 minutes to yield red crystals. After filtration, chromatography on silica gel (chloroform) allows the expected product to be isolated.

Melting Point: 180° C.

Elemental microanalysis:

|  | % C | % H | % N |
|---|---|---|---|
| calculated | 64.63 | 3.73 | 4.71 |
| found | 62.89 | 3.84 | 4.69 |

EXAMPLE 15

6-Nitro-3-(4-methoxyphenyl)-8H-thieno[2,3-b]pyrrolizin-8-one

A solution of 1 mmol of the compound obtained in Example 12 in 50 ml of nitromethane is stirred for 12 hours at ambient temperature and the reaction mixture is then poured into a 1M potassium hydroxide solution. After extracting with dichloromethane, the organic phases are dried over sodium sulphate, filtered and concentrated under reduced pressure. Chromatography on silica gel (chloroform) allows the expected product to be isolated.

EXAMPLE 16

6-Amino-3-(4-methoxymethyl)-8H-thieno[2,3-b]pyrrolizin-8-one

A solution containing 1 equivalent of the compound obtained in Example 14 in 30 ml of methanol and 100 mg of 10% palladium-on-carbon is heated for 2 hours at 40° C. After returning to ambient temperature, the reaction mixture is filtered over Celite and then concentrated under reduced pressure, allowing the expected product to be isolated.

EXAMPLE 17

6-Methoxy-3-(4-methoxyphenyl)-8H-thieno[2,3-b]pyrrolizin-8-one 1 equivalent of the compound obtained in Example 12 is stirred, at ambient temperature, into a solution of sodium methanolate. After 12 hours' reaction, the reaction mixture is concentrated under reduced pressure. The residue is taken up in dichloromethane; the organic phase is then washed with a saturated NaCl solution, dried over sodium sulphate and then concentrated under reduced pressure. Chromatography on silica gel (dichloromethane) allows the expected product to be isolated.

EXAMPLE 18

2-(Butyryloxy)-4-(8-oxo-8H-thieno[2,3-b]pyrrolizin-3-yl)phenyl butyrate 2.2 equivalents of butanoic anhydride are added dropwise to a solution of 1.7 mmol of the compound of Example 8 in 50 ml of tetrahydrofuiran. After one hour's reflux, and then cooling, a few drops of water and 50 ml of 5% sodium hydroxide are added to the reaction mixture. The organic phase is subsequently extracted, dried, filtered and then evaporated off under reduced pressure, allowing the expected product to be isolated.

Elemental microanalysis:

|  | % C | % H | % N |
|---|---|---|---|
| calculated | 65.23 | 4.99 | 3.30 |
| found | 65.11 | 4.93 | 4.02 |

EXAMPLE 19

2-Hydroxy-4-(8-oxo-8H-thieno[2,3-b]pyrrolizin-3-yl)phenyl pivalate

The procedure is as in Example 18, using 1,1-dimethylpropanoic anhydride as reagent.

Elemental microanalysis:

|  | % C | % H | % N |
|---|---|---|---|
| calculated | 65.38 | 4.66 | 3.81 |
| found | 65.18 | 4.69 | 3.73 |

EXAMPLE 20

2-(Acetoxy)-4-(8-oxo-8H-thieno[2,3-b]pyrrolizin-3-yl)phenyl acetate

The procedure is as in Example 18, using acetic anhydride as reagent.

Elemental microanalysis:

|  | % C | % H | % N |
|---|---|---|---|
| calculated | 62.11 | 3.56 | 3.81 |
| found | 62.18 | 3.53 | 3.97 |

EXAMPLE 21

4-(8-Oxo-8H-thieno[2,3-b]pyrrolizin-3-yl)-2-(propionyloxy)phenyl propionate

The procedure is as in Example 18, using propanoic anhydride as reagent.

Elemental microanalysis:

|  | % C | % H | % N |
|---|---|---|---|
| calculated | 63.78 | 4.33 | 3.54 |
| found | 63.50 | 4.29 | 3.51 |

EXAMPLE 22

3-[3(Benzyloxy)-4-methoxyphenyl]-8H-thieno[2,3-b]pyrrolizin-8-one

Preparation A: 2-[3-(Benzyloxy)-4-methoxypenyl] acetonitrile

Step 1: 3-Benzyloxy-4-methoxybenzaldehyde 1.2 equivalents of $K_2CO_3$ and 1.2 equivalents of benzyl bromide are added to a suspension of 0.33 mol of 3-hydroxy-4-methoxybenzaldehyde in 400 ml of methanol. After 24 hours' reflux, the reaction mixture is filtered while hot and the organic phase is then evaporated off under reduced pressure. The isolated residue is taken up in 300 ml of chloroform and then washed with water. After extraction, drying and filtration, evaporating off the organic phase under reduced pressure allows the expected product to be isolated.

Step 2: [3-(Benzyloxy)-4-methoxyphenyl]methanol

A solution of 0.35 mol of the compound obtained in Step 1 in 400 ml of methanol and 1.5 equivalents of sodium borohydride is stirred for 6 hours at ambient temperature and then 500 ml of acidified water are slowly added. The precipitate obtained is taken up in ether; the organic phase is subsequently extracted, dried, filtered and then evaporated off under reduced pressure, allowing the expected product to be isolated.

Step 3 : 2-Benzyloxy)-4-chloromethyl-1-methoxybenzene

A solution of 0.32 mol of the compound obtained in Step 2 and 1.2 equivalents of thionyl chloride in 300 ml of dioxane is stirred at ambient temperature. After 1 hour's reaction, 500 ml of water are added. The precipitate formed is filtered off, rinsed with water and then dried, allowing the expected product to be isolated.

Step 4: 2-[3-(Benzyloxy)-4-methoxyphenyl] acetonitrile

A solution of 0.22 mol of the compound obtained in Step 3 in 300 ml of acetonitrile and 1.1 equivalents of tetraethylammonium cyanide is stirred for one day at ambient temperature and then 500 ml of a 5% sodium hydrogen carbonate solution are added. The precipitate obtained is taken up in ether; the organic phase is then extracted, dried, filtered and evaporated off under reduced pressure, allowing the expected product to be isolated.

Elemental microanalysis:

|  | % C | % H | % N |
|---|---|---|---|
| calculated | 75.86 | 5.96 | 5.52 |
| found | 75.83 | 6.12 | 5.55 |

The product of Preparation A is then subjected to the reactions described in Example 1, Steps A to F, allowing the expected title product of the Example to be isolated.

Elemental microanalysis:

|  | % C | % H | % N |
|---|---|---|---|
| calculated | 71.30 | 4.42 | 3.62 |
| found | 71.52 | 4.67 | 3.77 |

EXAMPLE 23

3-[4-(Benzyloxy)-3-methoxyphenyl]-8H-thieno[2,3-b]pyrrolizin-8-one

Preparation B: 2-[4-(Benzyloxy)-3-methoxyphenyl] acetonitrile

The procedure is as in Preparation A, Steps 1 to 4, using 4-hydroxy-3-methoxybenzaldelhyde as substrate in Step 1.

Elemental microanalysis:

|  | % C | % H | % N |
|---|---|---|---|
| calculated | 75.86 | 5.96 | 5.52 |
| found | 75.62 | 6.02 | 5.88 |

The product of Preparation B is then subjected to the reactions described in Example 1, Steps A to F, allowing the expected title product of the Example to be isolated.
Elemental microanalysis:

|  | % C | % H | % N |
|---|---|---|---|
| calculated | 71.30 | 4.42 | 3.62 |
| found | 70.87 | 4.32 | 3.64 |

EXAMPLE 24

3-(4-Hydroxy-3-methoxyphenyl)8H-thieno[2,3-b]pyrrolizin-8-one

1mmol of the compound of Example 23 dissolved in an excess of hydrobromic acid in 33% acetic acid is stirred for 30 minutes at ambient temperature. After adding 100 ml of water, a precipitate is formed, which is filtered off and then dried. Chromatography on silica gel (ethyl acetate/hexane:1/2) allows the expected product to be isolated.

EXAMPLE 25

2-Methoxy-5-(8-oxo-8H-thieno[2,3-b]pyrrolizin-3-yl)phenyl acetate

The procedure is as in Example 18, using the compound of Example 24 as substrate and carrying out the reaction in acetic acid in the presence of acetic anhydride.
Elemental microanalysis:

|  | % C | % H | % N |
|---|---|---|---|
| calculated | 63.70 | 3.86 | 4.12 |
| found | 63.25 | 4.46 | 4.37 |

Pharmacological Study of Compounds of the Invention

EXAMPLE 26

In vitro cytotoxicity

Six cell lines were used:
2 murine leukaemias, P388 and L1210,
1 human non-small-cell lung carcinoma, A549,
1 human epidermoid carcinoma, KB-3-1, and the corresponding resistant line, KB-A 1, the multi-drug, resistance of which was produced using adriamycin (ADR),
1 human ovarian carcinoma, IGROV1.

The cells are cultured in RPMI 1640 complete culture medium containing 10% fetal calf serum, 2 mM glutamine, 50 units/ml of penicillin, 50 µg/ml of streptomycin and 10 mM Hepes, pH=7.4. The cells are distributed on microtitre plates and exposed to the cytotoxic compounds. The cells are then incubated for 2 days (P388, L1210) or 4 days (A549, KB-A1, KB-3-1, IGROV1). The number of viable cells is then quantified by means of a calorimetric assay, the Microculture Tetrazolium Assay (*Cancer Res.* 1987, 47, 939–942).

The results are expressed as $IC_{50}$, the concentration of cytotoxic agent that inhibits the proliferation of the treated cells by 50%. In these tests, the compound of Example 8 has the $IC_{50}$'s set out in the Table below:

| Compounds tested | $IC_{50}$ nM | | | | | |
|---|---|---|---|---|---|---|
|  | P388 | L1210 | A549 | KB-3-1 | KB-A1 | IGROV1 |
| Example 8 | 356 | 222 | 122 | 33 | 22 | 56 |

The compound of Example 8 has a more potent effect on the cells originating from human solid tumours than on the two murine leukaemias, which is a particularly surprising and interesting result.

EXAMPLE 27

Action on the cell cycle

L1210 cells are incubated for 21 hours at 37° C. in the presence of different concentrations of the products being tested. The cells are then fixed using 70% (v/v) ethanol, washed twice in PBS and incubated for 30 minutes at 20° C. in PBS containing 100 µg/ml of RNase and 50 µg/ml of propidium iodide. The results are expressed as the percentage of cells that have accumulated in the G2+M phase after 21 hours, compared to the control (control: 20%). At a concentration of 500 nM, the compound of Example 8 causes 80–90% of the cells to accumulate in the G2+M phase after 21 hours.

EXAMPLE 28

In vivo activity: anti-tumour activity of the compounds on the P388 leukaemia

Line P388 (murine leukaemia) was supplied by the National Cancer Institute (Frederick, U.S.A.). The tumour cells ($10^6$ cells) were inoculated on day 0 into the peritoneal cavity of female BDF1 mice (Iffa-Credo, France) weighing from 18 to 20 g (groups of 6 animals). The products were administered by the intraperitoneal route once per day for 4 days (D1–4) at the doses indicated.

The anti-tumour activity is expressed as % T/C:

$$\% \ T/C = \frac{\text{Median survival time of the treated animals}}{\text{Median survival time of the control animals}} \times 100$$

The compound of Example 8 is active from the 25 mg/kg dose and enables the survival of the treated animals to be increased by 70%.

EXAMPLE 29

In vivo activity: anti-tumour activity of the compounds on the IGROV1 ovarian carcinoma IGROV1 tumour cells ($10^7$ cells) were incubated on day 0 in the peritoneal cavity of nude BABL/C mice (groups of 5 animals). The products were administered by the intraperitoneal route once per week on days 4, 11 and 18. The anti-tumour activity is expressed as % T/C as defined hereinbefore. The compound of Example 8 is active at the 200 mg/kg dose and increases the survival of the treated animals by 60% (T/C=160%).

EXAMPLE 30

Pharmaceutical composition: tablets

| Formulation for the preparation of 1000 tablets each containing 10 mg | |
|---|---|
| Compound of Example 8 | 10 g |
| Hydroxypropyl cellulose | 2 g |
| Wheat starch | 10 g |
| Lactose | 100 g |
| Magnesium stearate | 2 g |
| Talc | 2 g |

What is claimed is:

1. A compound selected from those of formula (I):

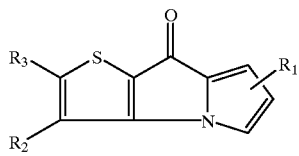

(I)

wherein:

R$_1$ is selected from the group consisting of hydrogen, halogen, linear or branched (C$_1$–C$_6$)alkyl, nitro, hydroxy, linear or branched (C$_1$–C$_6$)alkoxy, linear or branched (C$_1$–C$_6$)trihaloalkyl, linear or branched (C$_1$–C$_6$)trihaloalkoxy, and amino (optionally substituted by one or two linear or branched (C$_1$–C$_6$)alkyl, which may be identical or different, each independently of the other), R$_2$ represents optionally substituted aryl or optionally substituted heteroaryl, R$_3$ is selected from the group consisting of hydrogen, halogen, linear or branched (C$_1$–C$_6$)alkyl, nitro, hydroxy, linear or branched (C$_1$–C$_6$)alkoxy, linear or branched (C$_1$–C$_6$)trihaloalkyl, linear or branched (C$_1$–C$_6$)trihaloalkoxy, and amino (optionally substituted by one or two linear or branched (C$_1$–C$_6$)alkyl, which may be identical or different, each independently of the other), an isomer and a pharmaceutically-acceptable acid or base addition salt thereof, with the proviso that, when R$_1$ and R$_3$ simultaneously represent hydrogen, R$_2$ cannot represent phenyl or R$_2$ cannot represent phenyl substituted in the para position by bromine, chlorine, fluorine, methoxy, or hydroxy, it being understood that aryl means phenyl, naphthyl, dihydronaphthyl, tetrahydronaphthyl, indenyl or indanyl, that heteroaryl means mono- or bicyclic aromatic having 5 to 12 members and containing one, two, or three hetero atoms, which may be identical or different, selected from oxygen, nitrogen and sulphur, and that "optionally substituted" refers to aryl or heteroaryl as defined hereinbefore optionally substituted by one or more groups, which may be identical or different, each selected independently of the other(s) from halogen, linear or branched (C$_1$–C$_6$)alkyl, hydroxy, linear or branched (C$_1$–C$_6$)alkoxy, linear or branched (C$_1$–C$_6$)trihaloalkoxy, nitro, cyano, amino, linear or branched (C$_1$–C$_6$)alkylamino, di-(C$_1$–C$_6$)alkylamino in which each alkyl is linear or branched, linear or branched (C$_1$–C$_6$)acyl, aminocarbonyl (the amino moiety being optionally substituted by one or two linear or branched (C$_1$–C$_6$)alkyl, which may be identical or different), carboxy, linear or branched (C$_1$–C$_6$)alkoxycarbonyl, methylenedioxy, ethylenedioxy, linear or branched (C$_1$–C$_6$)alkylcarbonyloxy, and aryl (C$_1$–C$_6$)alkoxy in which the alkoxy is linear or branched.

2. A compound of claim 1, wherein R$_2$ represents phenyl substituted by at least one member selected from the group consisting of halogen, linear or branched (C$_1$–C$_6$)alkyl, nitro, cyano, hydroxy, linear or branched (C$_1$–C$_6$)alkoxy, linear or branched (C$_1$–C$_6$)trihaloalkoxy, amino, mono- or di-(C$_1$–C$_6$)alkylamino in which each alkyl is linear or branched, linear or branched (C$_1$–C$_6$)acyl, carboxy, linear or branched (C$_1$–C$_6$)-alkoxycarbonyl, methylenedioxy, ethylenedioxy, linear or branched (C$_1$–C$_6$)alkylcarbonyloxy, and aryl-(C$_1$–C$_6$)alkoxy in which alkoxy is linear or branched.

3. A compound of claim 1, wherein R$_2$ represents phenyl substituted by at least one group selected from hydroxy, linear or branched (C$_1$–C$_6$)alkoxy, and linear or branched (C$_1$–C$_6$)alkylcarbonyloxy.

4. A compound of claim 1, wherein R$_1$ represents hydrogen and R$_3$ represents hydrogen.

5. A compound of claim 1 which is 3-(3,4-dihydroxyphenyl)-8H-thieno[2,3-b]pyrrolizin-8-one.

6. A compound of claim 1 which is 2-methoxy-5-(8-oxo-8H-thieno[2,3-b]pyrrolizin-3-yl)phenyl acetate.

7. A method for treating a living body afflicted with cancer comprising the step of administering to the living body an amount of a compound of claim 1, which is effective for alleviation of said cancer.

8. A pharmaceutical composition useful in treating cancer comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 6,071,945
DATED : June 6, 2000
INVENTOR(S) : S. Rault, C. Enguehard, J.C. Lancelot, M. Robba, G. Atassi, A. Pierre, D.H. Caitnard P. Renard It is certified that error appears in the above-indentified patent and that said Letters Patent is hereby corrected as shown below:

Column 1, line 49: "nitro (group," should read:
-- nitro group, --. Page 2, line 2

Column 5, line 42: "-methophenyl)" should read:
-- -methoxyphenyl) --. Page 7, line 25

Column 6, line 18: "pyrrol)-" should read:
-- pyrrolyl)- --. Page 8, line 20

Column 9, line 39: "2,6Dibromo-2-(4-methoxyphenyl)-8-H-"
should read-- 2,6-Dibromo-2-(4-methoxyphenyl)-8H- --
Page 13, line 11

Column 10, line 62: "tetrahydrofuiran." should read:
-- tetrahydrofuran. --. Page 15, line 2

Column 11, line 62: "-methoxypenyl]" should read:
-- -methoxyphenyl] --. Page 16, line 6

Column 14, line 4: "calorimetric" should read:
-- colorimetric --. Page 19, line 6

Signed and Sealed this

First Day of May, 2001

Attest:

NICHOLAS P. GODICI

Attesting Officer   Acting Director of the United States Patent and Trademark Office